United States Patent [19]
Ullman et al.

[11] Patent Number: 6,016,711
[45] Date of Patent: Jan. 25, 2000

[54] MOBILE VEHICLE EMISSIONS SAMPLING SYSTEM

[75] Inventors: Terry L. Ullman; Cynthia C. Webb, both of San Antonio, Tex.

[73] Assignee: Southwest Research Institute, San Antonio, Tex.

[21] Appl. No.: 08/976,017

[22] Filed: Nov. 21, 1997

[51] Int. Cl.⁷ .................................................. G01N 1/00
[52] U.S. Cl. ............................................................ 73/863.03
[58] Field of Search ............................... 73/23.31, 23.32, 73/863.01–863.03, 864.73

[56] References Cited

U.S. PATENT DOCUMENTS

| | | | |
|---|---|---|---|
| 3,793,887 | 2/1974 | Anderson et al. | 73/863.03 |
| 3,986,386 | 10/1976 | Beltzer et al. | 73/28 |
| 4,348,732 | 9/1982 | Kreft | 364/571 |
| 4,586,367 | 5/1986 | Lewis | 73/116 |
| 4,727,746 | 3/1988 | Mikasa et al. | 73/23 |
| 5,129,257 | 7/1992 | Carduner et al. | 73/116 |
| 5,184,501 | 2/1993 | Lewis et al. | 73/863.01 |
| 5,218,857 | 6/1993 | Decker et al. | 73/23.31 |
| 5,419,178 | 5/1995 | Decker et al. | 73/23.31 |
| 5,469,731 | 11/1995 | Decker et al. | 73/863.03 |
| 5,639,957 | 6/1997 | Zarchy | 73/23.31 |
| 5,846,831 | 12/1998 | Silvis | 73/863.03 |

*Primary Examiner*—Robert Raevis
*Attorney, Agent, or Firm*—Baker & Botts, L.L.P.

[57] ABSTRACT

A sampling device for collecting exhaust samples that are proportional in amount to the total amount of exhaust during a given sampling period. A sample flow is pumped through the device, which has a filter for collecting particulates and a sample bag for collecting gas exhaust. The sampling device permits a baseline dilution air flow rate to be fixed by having a pair of parallel valves between the filter and the pump(s). During baselining, one valve is open and adjusted and one is closed and only dilution air flows through the device. Then, for sample acquisition, the second valve is also opened. A processing unit monitors the actual sample flow, compares it to a target flow rate, and adjusts the second valve as needed to maintain the desired proportionality.

22 Claims, 2 Drawing Sheets

MOBILE VEHICLE EMISSIONS SAMPLING SYSTEM

GOVERNMENT RIGHTS

The invention described herein was developed under Government Contract No. USDT-TPS6-SRI-410075-1115. The government may have certain rights in the invention.

TECHNICAL FIELD OF THE INVENTION

This invention relates to vehicle emissions testing, and more particularly to an exhaust sampling device that collects an exhaust sample whose volume over time is proportional to that of the total exhaust.

BACKGROUND OF THE INVENTION

Engine emissions testing has become increasing important as legislative pollution controls are enacted and public awareness of environmental concerns heightens. Typical test procedures involve acquiring a sample of the exhaust and then analyzing the sample for its constituents. The testing may be "real-time" such that the sample is analyzed as it is collected, or it may be collected remotely in time or location from the analysis.

A problem with many existing sampling techniques is that they rely on a laboratory setting and relatively large equipment to provide a sample whose quantity reflects changing engine speed and load and hence changing amounts of exhaust flow during the sample period. They do not permit the engine to be tested "in the field" under real-life operating conditions.

SUMMARY OF THE INVENTION

One aspect of the invention is a device for obtaining an exhaust sample of an engine exhaust flow. A probe inserted into the exhaust flow captures a portion of the exhaust flow. This portion is combined with a fixed rate of dilution air flow just upstream of a filter, which collects particulate emissions. Thus, the flow within the device is a mixture of dilution air and an exhaust portion. The flow is pulled through the sampling device by means of one or more pumps. Two parallel valves between the filter and the pump(s) are separately opened and adjusted. First, prior to sample acquisition, one valve is opened, adjusted, and set to provide a fixed dilution rate. During sample acquisition, the second valve is also opened and is adjusted as needed to maintain the proportionality of the exhaust portion. This second valve is controlled by a processing unit, which receives a sample rate measurement from a flow sensor, compares the measured rate to a target rate, and adjusts the second valve accordingly.

An advantage of the invention is that the exhaust portion of the output sample remains a constant proportion of the total flow rather than a fixed amount. A proportional sample may be collected during either steady-state or transient engine operation. Furthermore, the sampling device may be implemented so that it is small in size. It may be easily carried on an engine-powered vehicle and thus permits samples to be collected from a mobile engine.

DETAILED DESCRIPTION OF THE INVENTION

The following invention is directed to an engine exhaust sampling device that acquires an exhaust sample that is proportional in amount to the total amount of exhaust. In other words, the sample flow within the sampling device contains a constant proportion of the exhaust flow. To maintain this proportionality, the actual sample rate must varies as raw exhaust vary, which occurs in response to varying exhaust rates. For example, if a 1% proportion is specified, the rate of the sample flow will vary as the total exhaust rate varies, in order to maintain the 1% proportion.

The collection of a proportional sample permits emissions to be measured in terms of rates that are relative to engine operating conditions, fuel consumption, distance, and time. For example, emissions may be accurately quantitized in terms of grams per mile, or grams per horsepower hour, or grams per amount of fuel.

The sampling device may be used with any type of internal combustion engine, stationary or vehicular, during normal operating conditions. When used with a vehicle engine, the sampling device is carried on the vehicle as it travels.

The sampling device requires no modification to the engine. Its probe and sensors may be conveniently placed and removed.

The sampling device may be used regardless of the type of fuel used by the engine. For example, the fuel may be gasoline, diesel, or natural gas. As explained below, the sampling device may be used to acquire both particulate and gaseous samples.

To perform accurate emissions analysis, it is desirable to dilute the exhaust sample with air during the sampling process. Specifically, air dilution can prevent water condensation, reduce the temperature of the exhaust, or prevent or reduce the tendency of the exhaust constituents from reacting with each other. Thus, as explained below, the collected exhaust is diluted with a fixed amount of air, so that the flow within the sampling device is comprised of the proportional raw exhaust sample plus the fixed amount of dilution air.

Figure 1:
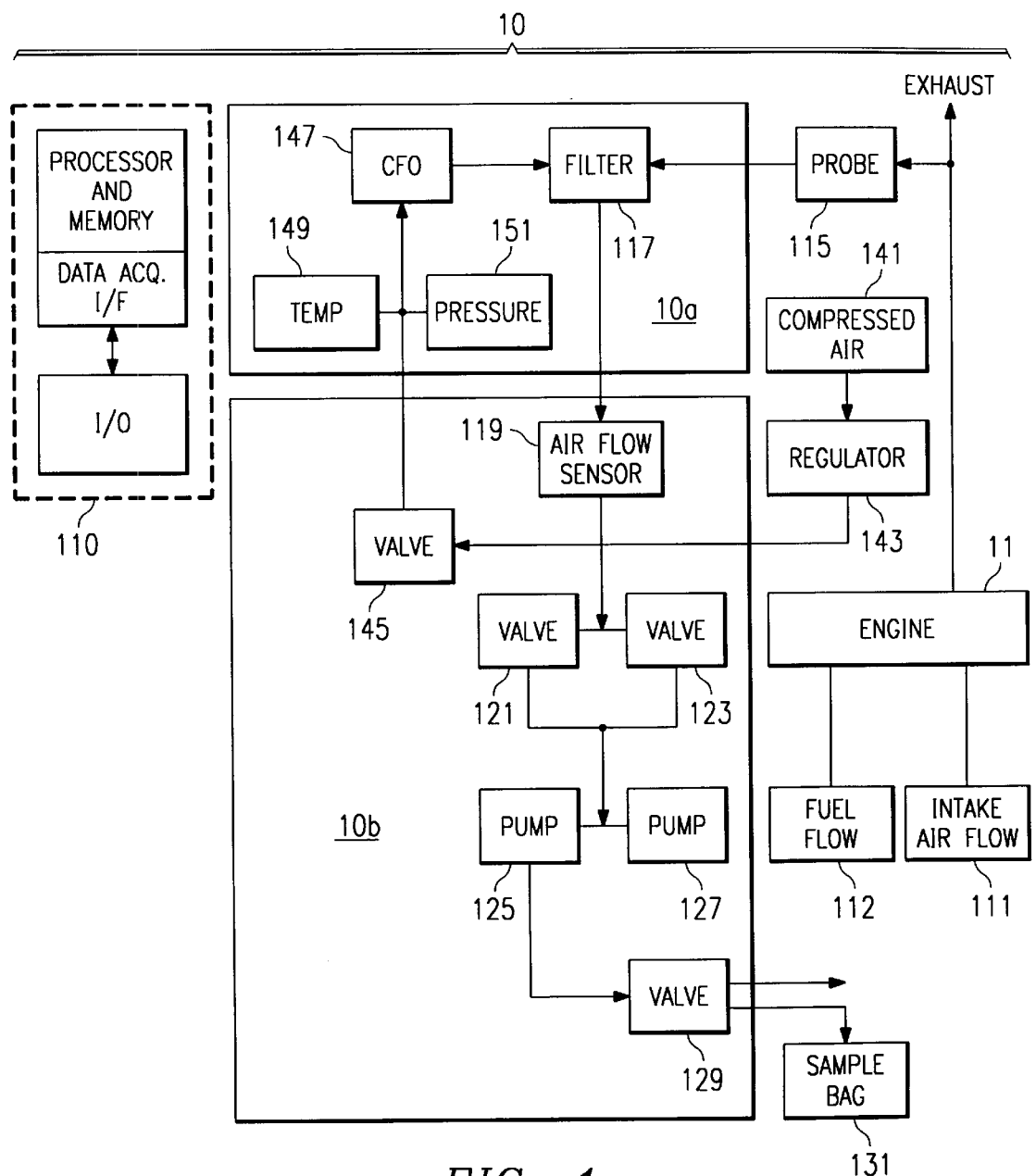
FIG. 1 is a block diagram of a sampling device in accordance with the invention.

FIG. 1 illustrates an exhaust sampling device 10 in accordance with the invention. As indicated, sampling device 10 may be configured as three separate modules, all capable of being placed in a mobile vehicle to test its engine emissions. These units comprise a processing unit 110, a probe module 10a and a control module 10b. Probe module 10a has a filter assembly 117 that receives both raw exhaust and dilution air. The diluted exhaust sample from filter assembly 117 is pulled into the control module 10b where various flow rate adjustments and measurements are made. Particulate emissions are collected at filter assembly 117 and gaseous emissions are collected at sample bag 131.

Processing unit 110 comprises at least a processor and memory, which execute and store programming for carrying out the sampling process steps described herein. The test operator inputs a desired sample proportion, which processing unit 110 uses to calculate a target sample rate. During sample acquisition, processing unit 110 receives measurement values of the actual sample rate. It adjusts the actual sample rate so that it matches the target sample rate. Various other corollary functions of processing unit 110 are described below.

Processing unit 110 may range in functionality from a dedicated controller-type unit to a general purpose computer. An interactive computer implementation is described below in connection with FIG. 2. In either case, processing unit 110 also has a data acquisition interface and appropriate input/output circuitry. An example of suitable data acquisition hardware is a National Instruments DaQCard. Electromechanical relays with independent non-latching relays for digital signal conditioning may be used in connection with valve and pump control signals.

Sampling device 10 operates on the principle that the mass flow into an engine will equal the mass flow out after combustion. Thus, if the engine's air and fuel intake are known, its exhaust flow is known. Accordingly, sampling device 10 has a mass air flow sensor 111 and a fuel flow sensor 112, which measure the air flow rate and the fuel flow rate respectively, at appropriate engine intake locations. From these two parameters, computer 110 estimates the exhaust flow. Any one of a number of various types of flowmeters could be used to measure air and fuel flow.

In other embodiments, fuel flow sensor 112 could be eliminated and the fuel flow provided to, or estimated by, processing unit 110. Or, both air flow sensor 111 and fuel flow sensor 112 could be eliminated, with the exhaust flow directly measured with an exhaust flow sensor or estimated. In any event, processing unit 110 acquires or determines, directly or indirectly, "exhaust flow measurements" as the exhaust flow varies during engine operation. The exhaust flow values are used to calculate the target sample rate, using the proportionality constant provided by the test operator.

A probe 115 is placed at an appropriate location at the engine exhaust, such as in the tailpipe of a vehicle. As explained below, the entry of raw exhaust into probe 115 and hence into sampling device 10 is controlled by valves 121 and 123 and pumps 125 and 127.

Another input to sampling device 10 is dry dilution air. In the embodiment of FIG. 1, the dilution air source is a compressed air reservoir 141, with a regulator 143 at its output. In other embodiments, the dilution air could be the output of an air pump. In any event, the dilution air flow is assumed to be a positive flow into sampling device 10. The flow of dilution air may be shut on or off with valve 145. The test operator uses regulator 143 to adjust the air flow rate, which is essentially constant during sample acquisition. Typically, the dilution air is adjusted prior to sample acquisition so as to not exceed 125 degrees Fahrenheit at filter assembly 117. However, this temperature is an accepted procedural limitation, not a limitation of sampling device 10.

The dilution air enters sampling device 10 at a dilution flow orifice 147. Preferably, orifice 147 is a critical flow orifice so that downstream variations in pressure do not affect the flow through orifice 147. A typical flow through orifice 147 is in the order of 1 kg/per hour when the dilution air pressure is in the range of about 200 to 300 kPa.

A temperature sensor 149 and pressure sensor 151 provide temperature and pressure measurements at critical flow orifice 147 to processing unit 110. From these measurements and from the specifications of critical flow orifice 147, processing unit 110 calculates an "actual dilution rate" into sampling device 10. If the actual dilution rate is not as desired, it can be adjusted using regulator 143. Other means for determining the actual dilution rate could be used, such as flow meters similar to those used elsewhere in sampling device 10.

Although various flow lines within sampling device 10 are not explicitly described, it should be understood that appropriate flow lines are used for the flow paths of the raw exhaust, the dilution air, and the mixture of raw exhaust and dilution air. Examples of suitable flow line materials are Teflon or stainless steel tubing. From probe 115, the raw exhaust and the dilution air enter filter assembly 117, which is comprised of a housing assembly containing at least one filter media, where they are mixed together. The result is a combined sample flow having an "actual sample rate". The sample flow is pulled through the filter media of filter assembly 117 to a mass air flow sensor 119. The filter media of filter assembly 117 captures particulate emissions. The mass of particulates on the filter media is the mass associated with the proportional exhaust sample. If desired, multiple items of filter media could be used in series or in parallel. Also, although filter assembly 117 combines mixing and filtering elements in a single assembly, separate mixing and filtering elements could be used.

After the sample flow is pulled through filter assembly 117, mass air flow sensor 119 measures the sample flow. This "actual sample rate" measurement is delivered to processing unit 110. Various other types of flowmeters could be used to measure the actual sample rate, with appropriate calculations to provide the desired units of measure.

After being pulled through mass air flow sensor 119, the sample flow is split into two parallel paths. Each path flows through a different valve 121 or 123. As explained below, valve 123 is manually adjusted to establish a baseline rate of dilution air only, during the engine-off state when there is no raw exhaust and only dilution air is flowing through the sampling device. Valve 123 is then fixed in its adjusted position and valve 121 is opened during the engine-on state. Valve 121 is adjusted by processing unit 110 to control the actual sample rate so as to maintain the desired sample proportion.

The parallel flow paths out of valves 121 and 123 are joined to create a single flow, which is then split to pumps 125 and 127. The use of dual pumps 125 and 127 permits fast response times without unduly increasing the volume of sample flow to be collected in sample bag 131. With regard to fast response times, the faster flow provided by the two pumps 125 and 127 means that as the engine's exhaust flow rate varies, the exhaust sample is collected quickly thereafter. However, with regard to sample volume, the use of dual pumps 125 and 127 provides a means for splitting the sample flow into two streams, thereby permitting a single pump's output to be used to collect the exhaust sample.

The portion of the exhaust flow through pump 127 is discarded. Alternatively, it could be delivered to real-time sample analysis system or to some other sample collection device. From pump 125, valve 129 controls whether the exhaust will be collected into a sample bag 131 or carried out a bypass exit and discarded if sample collection is not desired.

An example of a suitable sample bag 131 is a Tedlar bag, which is typically about 30×40 inches in size. A bag of this size can accumulate approximately 135 grams (approximately 4 cubic feet) of dilute sample. Thus, because about half the actual sample flow within sampling device 10 is discarded from pump 127, a typical sample flow provides about 270 grams during the sample period.

Each of the above-described valves 121, 129, and 145 may be implemented with on/off solenoids and controlled by processing unit 110. In the case of valve 121, which controls the variable exhaust rate, a varying pulse duty cycle of on/off signals may be used.

In typical operation, the sampling device 10 is first baselined. First, and prior to starting engine 11, the dilution air is turned on by opening valve 145. Valve 121 is closed, valve 123 is open, and pumps 125 and 127 are on. Regulator 143 is adjusted to provide an operator-specified actual dilution rate value as calculated by processing unit 110. Valve 123 is adjusted so that the actual sample rate measured by mass air flow sensor 119 is equal to the actual dilution rate. At this point, the sampling device is "balanced" so that no raw exhaust enters probe 115 and no dilution air is backflowing out from probe 115. Only dilution air is being pulled through sampling device 10. The result is a baseline flow of dilution air, which establishes a fixed baseline rate for sample acquisition.

After sampling device 10 is baselined, device 10 may be used to acquire an exhaust sample. A target sample rate is set, which is greater than the dilution air rate. This target sample rate may be calculated by processing unit 110 in response to a "proportionality constant" input to processing unit 110 by the test operator. The proportionality constant is the desired proportion of sample exhaust to total exhaust.

Now, engine 11 is turned on, such that it produces an exhaust flow. Now, valve 121 is turned on. Valve 123 remains open at the position obtained during "baselining". Processing unit 110 calculates the target sample rate from the proportionality constant and the actual exhaust flow. It compares this target sample rate to the actual sample rate. When the values do not match, it adjusts valve 121 accordingly. Thus, as the engine load or speed varies, and hence the exhaust flow, processing unit 110 adjusts valve 121 accordingly. The above-described calculating, comparing, and adjusting steps occur repeatedly during the sampling period, and could be triggered by various means such as a clock (periodically) or by changes in the exhaust flow (in response to an interrupt type of signal).

The sample acquisition may be immediately followed by a return of the target sample rate to the dilution air rate and closing of valve 121. Raw exhaust will no longer be pulled into sampling device 10 and the sampling device 10 will be cleared by a dilution air flow.

The exhaust sample may be transported or stored and analyzed for its constituents. Because the proportion of the sample to the total exhaust is known, the proportionality of each constituent, gaseous or particulate, can be determined. The collection and analysis of samples can be cumulative, and can represent varying engine load and speed.

The operator-specified proportionality constant is selected in light of various constraints. These constraints include the temperature at the filter assembly 117, the length of the test period, levels of raw exhaust generated during the test, characteristics of particulate emissions, restrictions of the flow capacity of pumps 125 and 127, and the capacity of the sample bag 131. Ideally, the proportionality constant is maximized within these constraints. Larger sample sizes tend to provide more accurate analysis. Thus, for example, if the filter temperature is sufficiently below a predetermined temperature, the operator might decide to increase the proportionality constant for a next sample. Sampling device 10 is generally configured for an exhaust flow rate of up to 2000 kg/hr and a typical sample rate might be less than 0.1% of that rate.

Figure 2:
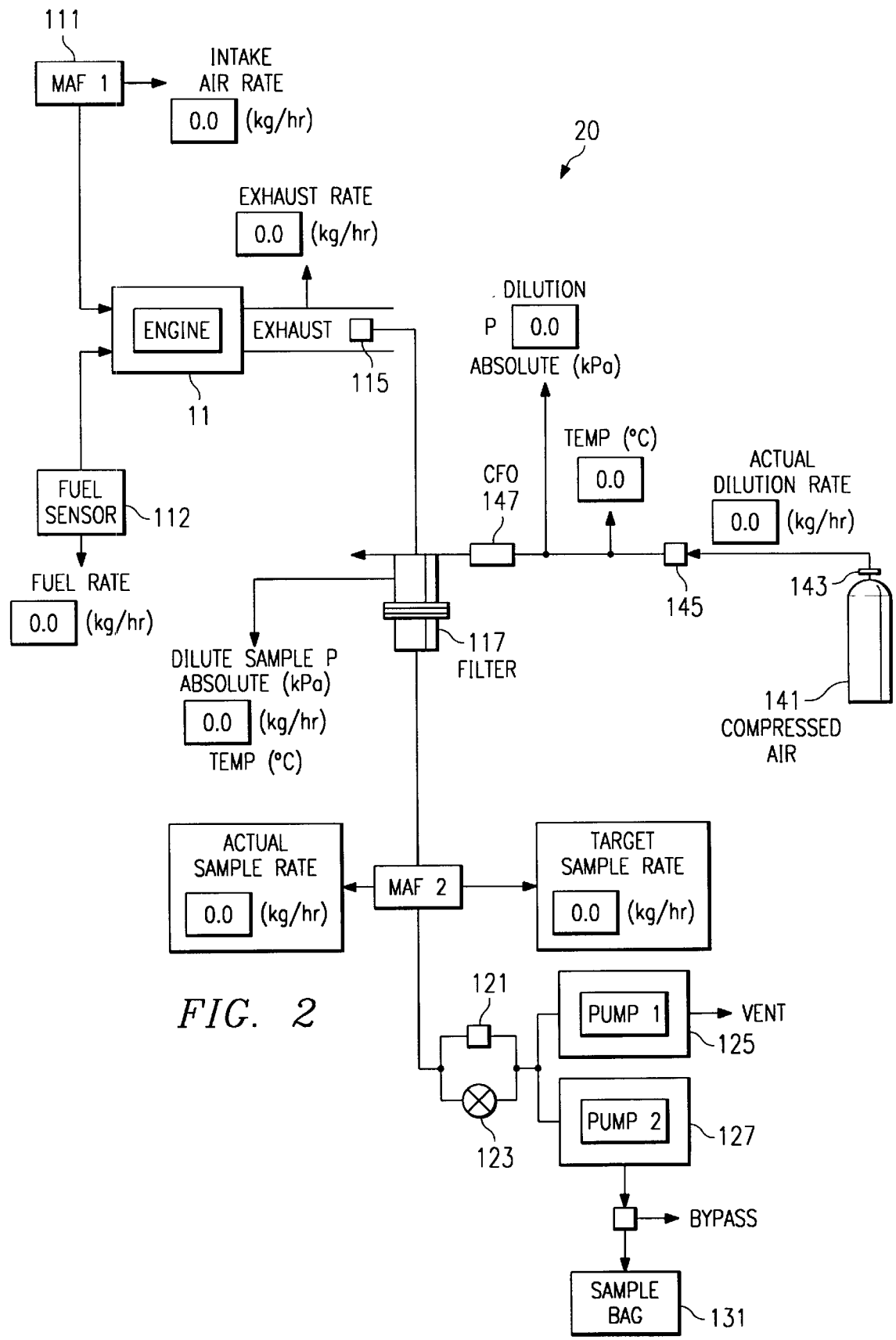
FIG. 2 illustrates a screen that is displayed when the sampling device of FIG. 1 is implemented with interactive computer programming.

FIG. 2 illustrates a screen 20, which is displayed when processing unit 110 includes a display. In this embodiment, sampling device 10 operates interactively with the test operator, by permitting the test operator to view and react to various displayed parameters. Screen 20 may also function as a control panel, which permits valves or other elements of sampling device 10 to be activated or adjusted by the test operator.

For the embodiment of FIG. 2, processing unit 110 may be implemented with a general purpose computer, such as a laptop-type personal computer. Suitable programming may be implemented with the LabView programming language.

As illustrated in FIG. 2, processing unit displays the "target sample rate" value, as well as other parameter values. During baselining, the test operator sets the target sample rate so that it equals a desired fixed dilution air rate. The operator may then simply read screen 20 to determine whether the actual dilution rate, the target dilution rate, and the actual sample rate are all equal. If not, the operator may adjust regulator 143 or valve 123 or both. During sample acquisition, the target sample rate is the sum of the fixed dilution rate and the rate of the exhaust flow entering into probe 115. As described above, the variable exhaust rate is calculated from the proportionality constant and a current exhaust rate value. The target sample rate is recomputed and displayed as the engine load, and hence the exhaust flow rate, vary.

The above-described embodiment uses two parallel valves 121 and 123, one of which is fixed during baselining and the other of which is computed controlled during sample acquisition. Such a configuration is useful when the valves are to be adjusted by different means, such as manually (for baselining) versus by computer (during sample acquisition). However, in other embodiments, the parallel valves could be replaced by a single valve. Both could be computer-controlled so that during baselining, it is adjusted to determine the baseline flow and then permitted to vary to maintain the proportional flow of exhaust sample. In either case, the invention accommodates a two-phase flow adjustment, a first phase to establish the baseline and a second phase to acquire the exhaust samples.

Other Embodiments

Although the present invention has been described in detail, it should be understood that various changes, substitutions, and alterations can be made hereto without departing from the spirit and scope of the invention as defined by the appended claims.

We claim:

1. A device for collecting an exhaust sample of an engine exhaust flow, comprising:

a probe for collecting a proportional amount of said exhaust flow;

a flow line for containing said exhaust sample, wherein said flow line has a dilution air orifice that receives a flow of dilution air, such that said exhaust sample is comprised of said proportional amount and said dilution air;

a flow sensor that measures the flow of said exhaust sample along said flow line;

at least one pump at the output end of said flow line, said at least one pump operable to said transport said exhaust sample along said flow line;

at least one valve on said flow line, between said flow sensor and said at least one pump;

an output port for said exhaust sample, said port located on said flow line downstream of said at least one valve; and a processing unit programmed to repeatedly perform the following: calculate a target exhaust flow value so as to maintain said proportional amount as said engine operates, receive measurements from said flow sensor, interpret said measurements to provide an actual sample flow value; compare said target exhaust flow value to said actual sample flow value, and to adjust said at least one valve in response to the comparison;

wherein said target exhaust flow value is the sum of a fixed baseline flow of dilution air and a variable flow of said proportional amount.

2. The device of claim 1, wherein said at least one pump is a pair of pumps, and wherein said flow line is split to said pumps such that said pumps operate in parallel.

3. The device of claim 1, further comprising a dilution air source.

4. The device of claim 3, wherein said dilution air source is a compressed air container.

5. The device of claim 1, wherein said dilution air orifice is a critical flow orifice.

6. The device of claim 1, wherein said processing unit is further programmed to calculate said target exhaust flow value from an exhaust proportionality constant.

7. The device of claim 1, further comprising a filter on said flow line for capturing particulates from said exhaust sample.

8. The device of claim 1, further comprising at least one sensor for providing exhaust flow measurements from said engine to said processing unit, and wherein said target exhaust flow value is based on said exhaust flow measurements.

9. The device of claim 8, wherein said at least one sensor is an exhaust flow sensor.

10. The device of claim 8, wherein said at least one sensor is an intake air flow sensor.

11. The device of claim 1, wherein said at least one valve is a pair of parallel valves, and wherein said computer is programmed to adjust only one of said valves.

12. A method of collecting an exhaust sample from an exhaust flow of an engine; comprising the steps of:

establishing a fixed flow of dilution air;

combining a portion of said exhaust flow with said flow of dilution air, such that said exhaust sample is comprised of said portion and said dilution air;

measuring the actual flow of said exhaust sample;

calculating a target flow, by using values representing a current flow of said exhaust, a specified proportionality constant of said exhaust, and said fixed flow of dilution air;

comparing said actual flow with said target flow;

adjusting the flow of said exhaust sample in response to said comparing step such that said actual flow matches said target flow; and collecting at least part of said exhaust sample.

13. The method of claim 12, wherein said collecting step is performed by filtering said exhaust sample through a particulate filter.

14. The method of claim 12, wherein said collecting step is performed by collecting said exhaust sample in a sample bag.

15. The method of claim 12, wherein said establishing step is performed using a computer programmed to receive dilution air flow measurements and measurements representing said actual flow, and to display values representing these measurements.

16. The method of claim 12, wherein said calculating and comparing steps are performed using a computer programmed to receive exhaust flow measurements representing said current flow of said exhaust and to calculate said target flow.

17. A method of collecting an exhaust sample from an exhaust flow of an engine; comprising the steps of:

establishing a fixed flow of dilution air, by pumping said dilution air through at least one valve, said valve being adjusted to provide said flow;

opening said at least one valve;

combining a portion of said exhaust flow with said flow of dilution air, such that said exhaust sample is comprised of said portion and said dilution air;

measuring the actual flow of said exhaust sample;

calculating a target flow, by using a value representing a current flow of said exhaust, a specified proportionality constant of said exhaust, and said fixed flow of dilution air;

comparing said actual flow with said target flow;

adjusting the flow of said exhaust sample in response to said comparing step such that said actual flow matches said target flow; and collecting at least part of said exhaust sample.

18. The method of claim 17, wherein said collecting step is performed by filtering said exhaust sample through a particulate filter.

19. The method of claim 17, wherein said collecting step is performed by collecting said exhaust sample in a sample bag.

20. The method of claim 17, wherein said establishing step is performed using a computer programmed to receive dilution air flow measurements and measurements representing said actual flow, and to display values representing these measurements.

21. The method of claim 17, wherein said calculating and comparing steps are performed using a computer programmed to receive exhaust flow measurements representing said current flow of said exhaust and to calculate said target flow.

22. The method of claim 17, wherein said at least one valve is a pair of valves, such that said establishing step is performed by opening and closing a first valve during said establishing step, and said opening step is performed by opening a second valve.

* * * * *